(12) United States Patent
Mehta

(10) Patent No.: US 10,492,730 B1
(45) Date of Patent: Dec. 3, 2019

(54) DETERMINING RELIABILITY FOR ECG DATA USING SIGNAL-TO-NOISE RATIO

(71) Applicant: Preventice Solutions, Inc., Rochester, MN (US)

(72) Inventor: Pooja Rajiv Mehta, Austin, TX (US)

(73) Assignee: Preventice Solutions, Inc., Rochester, MN (US)

( * ) Notice: Subject to any disclaimer, the term of this patent is extended or adjusted under 35 U.S.C. 154(b) by 0 days.

(21) Appl. No.: 16/298,724

(22) Filed: Mar. 11, 2019

(51) Int. Cl.
*A61B 5/04* (2006.01)
*A61B 5/00* (2006.01)
*A61B 5/0456* (2006.01)

(52) U.S. Cl.
CPC ........ *A61B 5/7221* (2013.01); *A61B 5/04012* (2013.01); *A61B 5/0456* (2013.01); *A61B 5/0006* (2013.01); *A61B 5/721* (2013.01); *A61B 5/7235* (2013.01)

(58) Field of Classification Search
CPC . A61B 5/7221; A61B 5/04012; A61B 5/0456; A61B 5/0006; A61B 5/721; A61B 5/7235
See application file for complete search history.

(56) References Cited

U.S. PATENT DOCUMENTS

| 5,749,367 A * | 5/1998 | Gamlyn | A61B 5/0006 600/509 |
| 2007/0203418 A1 * | 8/2007 | Starc | A61B 5/04525 600/509 |
| 2012/0277611 A1 * | 11/2012 | Schneider | A61B 5/0456 600/521 |

* cited by examiner

*Primary Examiner* — Lindsey G Wehrheim
(74) *Attorney, Agent, or Firm* — Patterson + Sheridan, LLP

(57) ABSTRACT

Techniques for determining reliability of electrocardiogram (ECG) data are disclosed. ECG data, including waveform data relating to a detected heartbeat for a patient, is received. A peak amplitude associated with an R-wave in the waveform data is determined. First and second baseline regions in the waveform data are identified. The first baseline region precedes the R-wave and the second baseline region follows the R-wave. A signal-to-noise ratio (SNR) is determined, based on the peak amplitude, the first baseline region, and the second baseline region. A confidence metric relating to the waveform data is determined, based on the determined SNR. The confidence metric is used in medical treatment related to the patient.

20 Claims, 10 Drawing Sheets

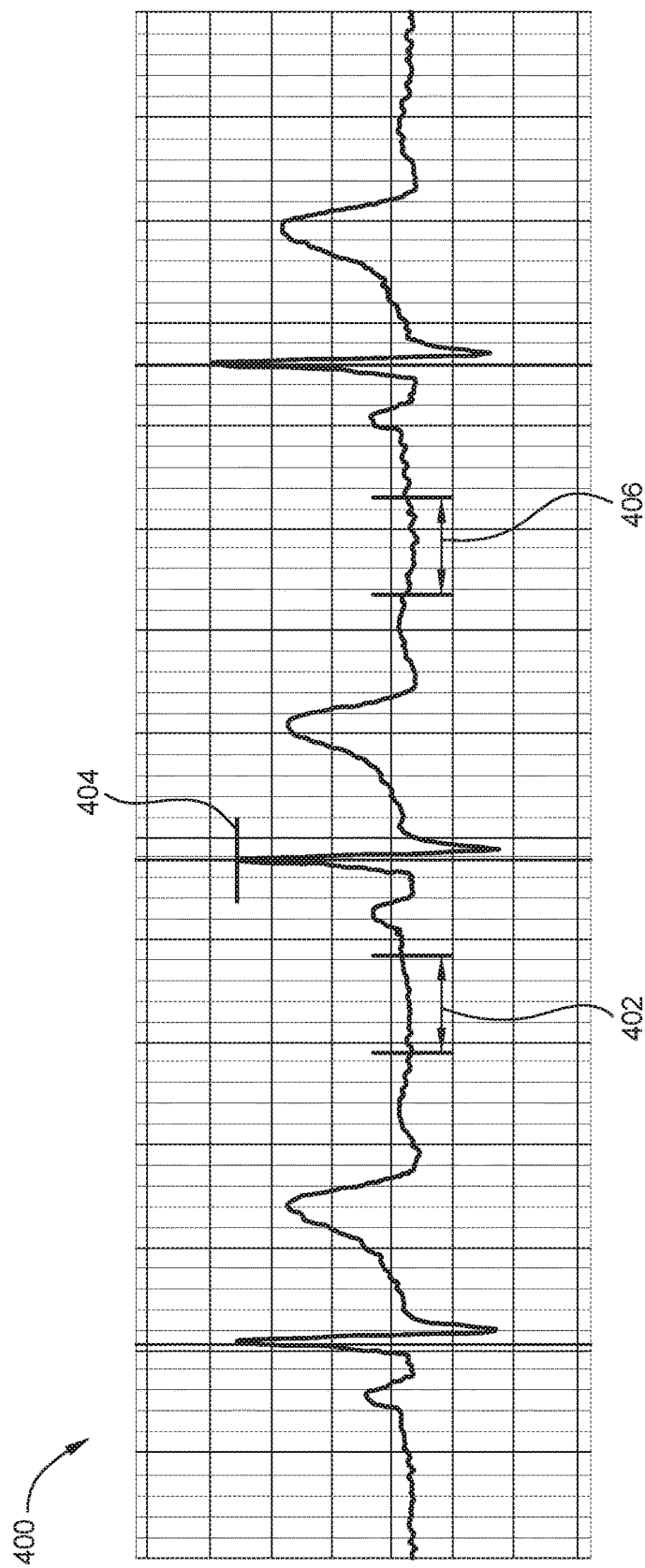

DETERMINING RELIABILITY FOR ECG DATA USING SIGNAL-TO-NOISE RATIO

BACKGROUND

Portable monitoring devices for collecting biometric data are becoming increasingly common in diagnosing and treating medical conditions in patients. Mobile cardiac telemetry (MCT), which can be used to record electrocardiogram (ECG) data for patients, is one example of this. MCT empowers physicians with valuable information regarding the occurrence and regularity of a variety of heart conditions and irregularities.

Processing ECG data, however, can be challenging. For example, ECG data may be inaccurate due to problems in collecting the data. This can lead to errors in identifying and classifying heartbeats in the ECG data. Further, this can lead to problems in diagnosing irregular or potentially dangerous heart conditions using the ECG data, and can lead to difficulties in identifying and treating these conditions.

BRIEF DESCRIPTION OF THE DRAWINGS

So that the manner in which the above-recited features of the present disclosure can be understood in detail, a more particular description of the disclosure, briefly summarized above, may be had by reference to embodiments, some of which are illustrated in the appended drawings. It is to be noted, however, that the appended drawings illustrate only typical embodiments of this disclosure and are therefore not to be considered limiting of its scope, for the disclosure may admit to other equally effective embodiments.

FIGS. 4A-C illustrate electrocardiogram (ECG) data, according to one embodiment described herein.

To facilitate understanding, identical reference numerals have been used, where possible, to designate identical elements that are common to the figures. It is contemplated that elements disclosed in one embodiment may be beneficially utilized on other embodiments without specific recitation.

DESCRIPTION OF EXAMPLE EMBODIMENTS

Overview

Figure 1:
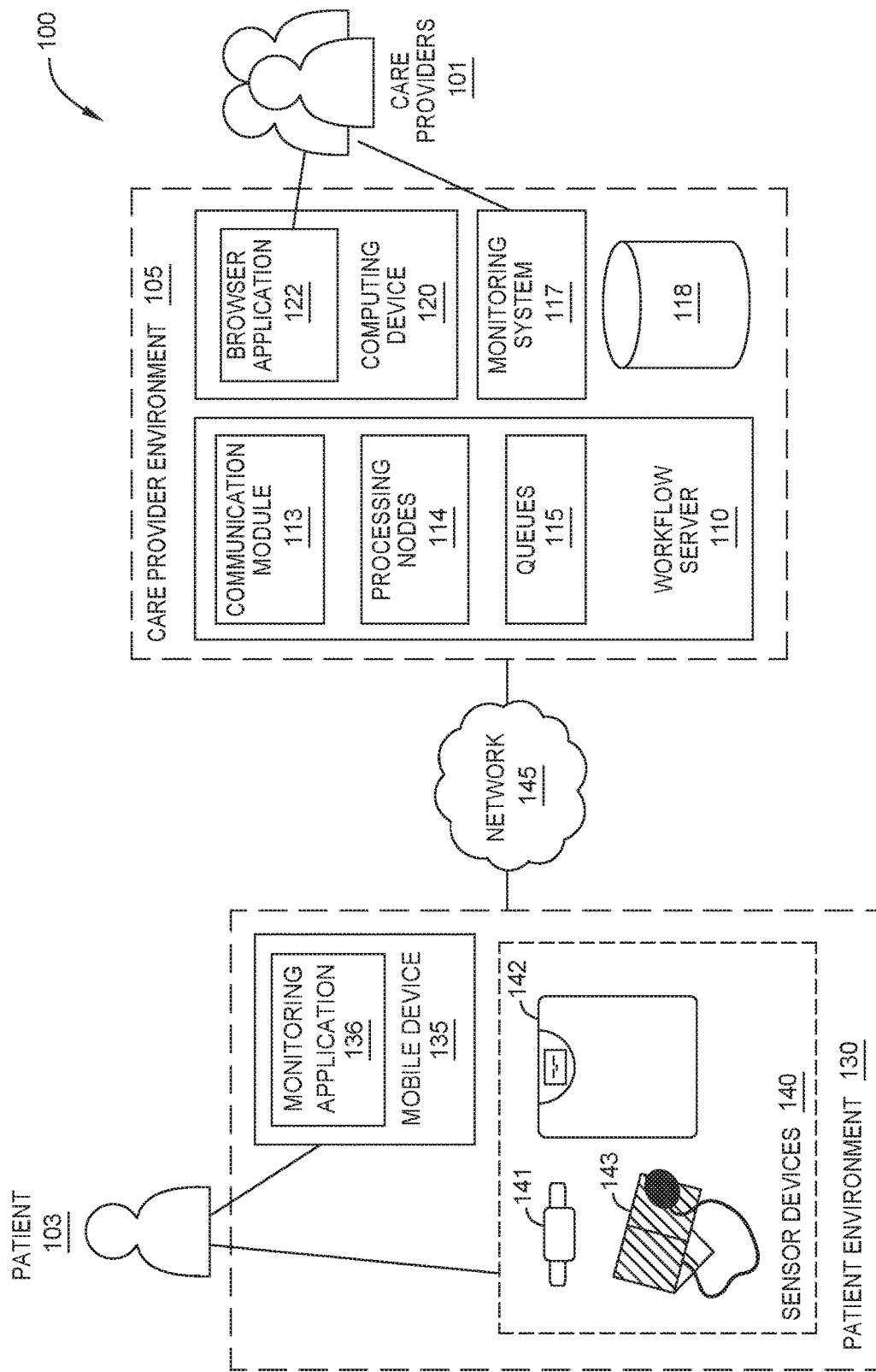
FIG. 1 illustrates an example computing environment, according to one embodiment described herein.

One embodiment provides a computer-implemented method for determining reliability of electrocardiogram (ECG) data. The method includes receiving ECG data including waveform data relating to a detected heartbeat for a patient. The method further includes determining a peak amplitude associated with an R-wave in the waveform data, relating to the heartbeat. The method further includes identifying a first baseline region in the waveform data and a second baseline region in the waveform data. The first baseline region relates to the heartbeat and precedes the R-wave and the second baseline region relates to the heartbeat and follows the R-wave. The method further includes determining a signal-to-noise ratio (SNR) for the waveform data relating to the heartbeat, based on the peak amplitude, the first baseline region, and the second baseline region. The method further includes determining a confidence metric relating to the waveform data, based on the determined SNR. The method further includes using the confidence metric in medical treatment related to the patient.

Further embodiments provide a computer program product for determining reliability of ECG data. The computer program product includes a computer-readable storage medium having computer-readable program code embodied therewith, the computer-readable program code executable by one or more computer processors to perform an operation. The operation includes receiving ECG data including waveform data relating to a detected heartbeat for a patient. The operation further includes determining a peak amplitude associated with an R-wave in the waveform data, relating to the heartbeat. The operation further includes identifying a first baseline region in the waveform data and a second baseline region in the waveform data. The first baseline region relates to the heartbeat and precedes the R-wave and the second baseline region relates to the heartbeat and follows the R-wave. The operation further includes determining a SNR for the waveform data relating to the heartbeat, based on the peak amplitude, the first baseline region, and the second baseline region. The operation further includes determining a confidence metric relating to the waveform data, based on the determined SNR. The operation further includes using the confidence metric in medical treatment related to the patient.

Further embodiments provide a system. The system includes a processor and a memory storing a program, which, when executed on the processor, performs an operation. The operation includes receiving ECG data including waveform data relating to a detected heartbeat for a patient. The operation further includes determining a peak amplitude associated with an R-wave in the waveform data, relating to the heartbeat. The operation further includes identifying a first baseline region in the waveform data and a second baseline region in the waveform data. The first baseline region relates to the heartbeat and precedes the R-wave and the second baseline region relates to the heartbeat and follows the R-wave. The operation further includes determining a SNR for the waveform data relating to the heartbeat, based on the peak amplitude, the first baseline region, and the second baseline region. The operation further includes determining a confidence metric relating to the waveform data, based on the determined SNR. The operation further includes using the confidence metric in medical treatment related to the patient.

EXAMPLE EMBODIMENTS

Electrocardiogram (ECG) data collected using mobile cardiac telemetry (MCT) can be analyzed to detect heartbeats and classify those heartbeats (e.g., determine the type of heartbeat). Generally, ECG data includes waveform data identifying electrical activity relating to patient heart activity. ECG data can be captured by service providers, annotated, and summarized into patient-specific reports for clinicians. The growing popularity of MCT results in a need for high-performance algorithms to analyze and classify the collected data.

For example, R-R intervals in the ECG data can be identified to detect heartbeats, and the ECG data relating to the identified heartbeats can be analyzed to classify the heartbeats and identify potentially irregular heartbeats and cardiac issues. These classifications can then be used to provide alerts to patients and care providers. This can be further used to provide medical treatment to patients.

But the collected ECG data may not always be reliable. For example, an ECG signal may include noise, resulting in a low signal-to-noise ratio (SNR). The SNR for a sample of ECG data can be determined in different ways. In one embodiment, the SNR for a detected heartbeat in ECG data is computed using the amplitude of the R wave associated with the detected heartbeat, along with the amplitude of surrounding baseline regions. In an embodiment, the SNR can be compared with a threshold to determine a confidence level in detection and classification of the heartbeat.

ECG data with low SNR is likely to be harder to use in diagnostic applications. For example, it is likely to be harder for a doctor or other care provider to diagnose cardiac issues using ECG data with a low SNR. Further, automated heartbeat detection and classification algorithms may be less accurate when analyzing ECG data with a low SNR. Thus, identifying SNR for ECG data can allow an automated MCT system to estimate the reliability of and usability of incoming ECG data. A system can then filter out less reliable data (e.g., filtering out less reliable data in favor of more reliable data), give less credence to less reliable data (e.g., give less weight to less reliable data when diagnosing cardiac abnormalities), or take steps to increase the reliability of the data (e.g., providing feedback to a patient or care provider to improve the collection of the ECG data).

Patient Care Environment

FIG. 1 illustrates an example computing environment 100, according to one embodiment described herein. As shown, the computing environment 100 may include a care provider environment 105 and a patient environment 130, each connected to one another via a network 145. The care provider environment 105 and the patient environment 130 allow a care provider 101 (e.g., a technician, nurse, physician, etc.) to monitor biometric data generated by the patient 103.

The care provider environment 105 includes a workflow server 110, a computing device 120, monitoring system 117 and data repository 118. Each of the workflow server 110, the computing device 120, and the monitoring system 117 may be a physical computing system or a virtual computer instance (e.g., executing in a cloud computing platform). A care provider 101 may use the computing device 120 to access (e.g., via a browser application 122, a native application on device 120, etc.) a user interface (UI) hosted by the monitoring system 117.

Of note, although shown as a single entity, the data repository 118 can represent multiple, separate data stores (e.g., relational databases). Moreover, these data stores can span multiple computing nodes. To this end, the separate data stores could be made to function as a single data store (e.g., through data replication techniques and through the use of load balancers). As such, the data repository 118 is representative of any sort of data store on any number of computing systems, consistent with the functionality described herein.

Additionally, although not shown, the data repository 118 may store data from and/or service requests from various other entities, such as third party applications, partners and affiliates, electronic medical record systems, external monitoring devices and products, analytics engines, data consolidator applications and so on. More generally, it is contemplated that the data repository 118 and, more generally, other elements within the care provider environment 105, can interact with any number of different data originators and receipts, consistent with the functionality described herein. As such, the computing environment 100 is provided merely for illustrative purposes only and without limitation.

The workflow server 110 includes applications and data executed to identify and handle health events corresponding to the patient 103. As shown, workflow server 110 includes a communication module 113, processing nodes 114, and queues 115. In one embodiment, the processing nodes 114 are software code or applications that perform a predetermined task or action on received data (e.g., health events). The workflow server 110 evaluates data received from the patient environment 130 using a set of interconnected processing nodes 114 and the queues 115 which form a workflow. As the biometric data or health events are received from the patient environment 130, the workflow may classify (or reclassify) the data to identify a type of the health event—e.g., presentation or notification to patient/care provider, suppression, classification, aggregation, computation, prioritization/triage, and the like. For example, different types of data received from the patient environment 130 may trigger different types of health events—e.g., an irregular heartbeat may trigger a cardiac event, while a signal indicated an electrode has become detached triggers a maintenance event. In one embodiment, at least one sensor device 140 within the patient environment 130 or a monitoring application 136 installed as part of a mobile device 135 within the patient environment 130 may have performed an initial classification of the data or health events. Nonetheless, the workflow server 110 may evaluate the biometric data (or maintenance data) to confirm that this initial classification was correct.

Each type of health event may take a different path through the workflow. That is, different health events may traverse the processing nodes 114 and the queues 115 using different paths. For example, a cardiac event may be evaluated using different processing nodes 114 in the server 110 than a maintenance event. Furthermore, paths through the workflow for the same health event may differ based on a variety of factors such as the severity of the health event, age of the patient 103, other symptoms exhibited by the patient 103, medication taken by the patient 103, and the like. For example, a high priority cardiac event may skip one or more of the processing nodes 114 or the queues 115 and be immediately displayed to the care provider 101 using the monitoring system 117.

The communication module 113 permits the workflow server 110 to receive the data from the patient environment 130 and transmit data to the care providers 101. The communication module 113 may receive data from the at least one sensor device 140 which is used to identify a health event and a corresponding path through interconnected ones of the processing nodes 114 and the queues 115. The communication module 113 helps the care providers 101 complete the workflow by use of the monitoring system 117 and the computing device 120. Moreover, in addition to receiving the data from the patient environment 130, the communication module 113 may enable the workflow server 110 to transmit requests or instructions to the patient environment 130 such as asking the patient 103 if she has any symptoms or instructing the patient 103 to reattach a disconnected electrode (not shown) of the at least one sensor device 140.

In one embodiment, a path used by a health event to traverse the workflow server 110 may include processing nodes 114 that process the health event without user intervention as well as the processing nodes 114 that require input from the care providers 101. For example, one of the processing nodes 114 may filter or screen a health event to determine what queue to place the event, compare the event to one or more rules to determine an action to perform, or store the event. Alternatively, others of the processing nodes 114 may require the care provider 101 to perform an action or provide instructions. For example, the monitoring system 117 may generate a user interface (UI) for a health event which is then displayed to the care provider 101 by the browser application 122. Once the care provider 101 performs an action (e.g., confirms the classification of the event or agrees with an action suggested by the workflow server 110), the remaining operations of the workflow are performed—e.g., send a notification to the patient 103, log the event in the history of the patient 103, route the event to a different one of the care providers 101, reclassify the health event (if the care provider 101 indicated the initial classification was incorrect), or prioritize or triage the health event.

With continued reference to FIG. 1, the patient environment 130 includes the mobile device 135 and the at least one sensor device 140. The mobile device 135 includes the monitoring application 136 which permits communication between the at least one sensor device 140 and the care provider environment 105 via the network 145. The monitoring application 136 may configure the at least one sensor device 140 (e.g., IoT devices) to monitor biometric data of the one or more patient 103 as specified by a care plan. For example, the monitoring application 136 could configure logic on a heart rate monitoring device worn by the patient to monitor the patient's heart rate. In turn, the monitoring application 136 can send the heart rate data to the workflow server 110 which determines if a heath event is triggered, and if so, executes a workflow to process the event as described above. In another embodiment, the heart rate monitoring device, upon detecting that a threshold condition has been satisfied, could generate and transmit a health event to the mobile device 135, which in turn transmits the health event to the workflow server 110 for processing. However, in other embodiments, some of the tasks performed by the workflow server 110 may be performed by the mobile device 135. That is, the workflow may include tasks performed by the mobile device 135 or the at least one sensor device 140 as well as tasks performed by the workflow server 110.

In one embodiment, the monitoring application 136 receives environmental data from the at least one sensor device 140. Generally, the environmental data informs the monitoring application 136 of environmental conditions in an area proximate to the at least one sensor device 140 and the user—e.g., a room in which the user is located. For example, the at least one sensor device 140 may detect an air quality or pollen count for the patient 103 having a respiratory ailment. In another example, the at least one sensor device 140 may track the user's movements or actions in an environment such as how many times at night the patient 103 goes to the bathroom or if the patient 103 is tossing and turning at night. This environmental data can then be used by the monitoring application 136 by itself, or in combination with the biometric data, to trigger health events which are processed by the workflow server 110.

In one embodiment, the monitoring application 136 may use an output device (e.g., a display or audio system) on the mobile device 135 to provide information to the patient 103. For example, when executing a workflow, one of the processing nodes 114 may ask the patient 103 if she is experiencing any symptoms. To obtain feedback from the patient 103, the monitoring application 136 may display a user interface (UI) on the mobile device 135 which permits the patient 103 to list symptoms. Moreover, the monitoring application 136 may also display general information related to a care plan or the at least one sensor device 140 such as the patient's heart rate or weight, status of the at least one sensor device 140, etc.

In one embodiment, the at least one sensor device 140 interacts with the monitoring application 136 and assists the patient 103 in reporting patient vitals and other information to the care provider environment 105. As shown, the at least one sensor device 140 may include a body sensor 141, a weighing scale 142, and a blood pressure cuff 143. Each of the at least one sensor device 140 may capture different vitals of the patient 103. For example, when applied to a body of patient 103, the body sensor 141 captures biometric data (e.g., heart rate, ECG data, etc.) in real-time. In addition, each of the at least one sensor device 140 may be configured to transmit body-related metrics electronically to the monitoring application 136 on the mobile device 135. In turn, the monitoring application 136 sends the captured metrics to the workflow server 110 which can be used to trigger health events which are processed using the processing nodes 114 and the queues 115.

In one embodiment, upon detecting an observation threshold has been reached, the at least one sensor device 140 performs an initial classification of the health event. In a particular embodiment, the mobile device 135 is configured to perform the initial classification of the health event. For example, the body sensor 141, upon detecting that ECG data collected from the patient 103 indicates an erratic heart behavior, could classify the health event as a cardiac event. This initial classification of the health event, along with the relevant ECG data (e.g., ECG data including a predetermined length of time before and after the event), could be transmitted to the mobile device 135 (e.g., over a Bluetooth® communications link) and the monitoring application 136 subsequently forwards the ECG data and the health event data on to the workflow server 110 over the network 145 (e.g., the Internet). Alternatively, instead of classifying the data, the monitoring application 136 may forward the raw, unprocessed sensor data to the workflow server 110 which uses one of the processing nodes 114 to identify and classify health events which are then processed in the workflow server 110.

Figure 2:
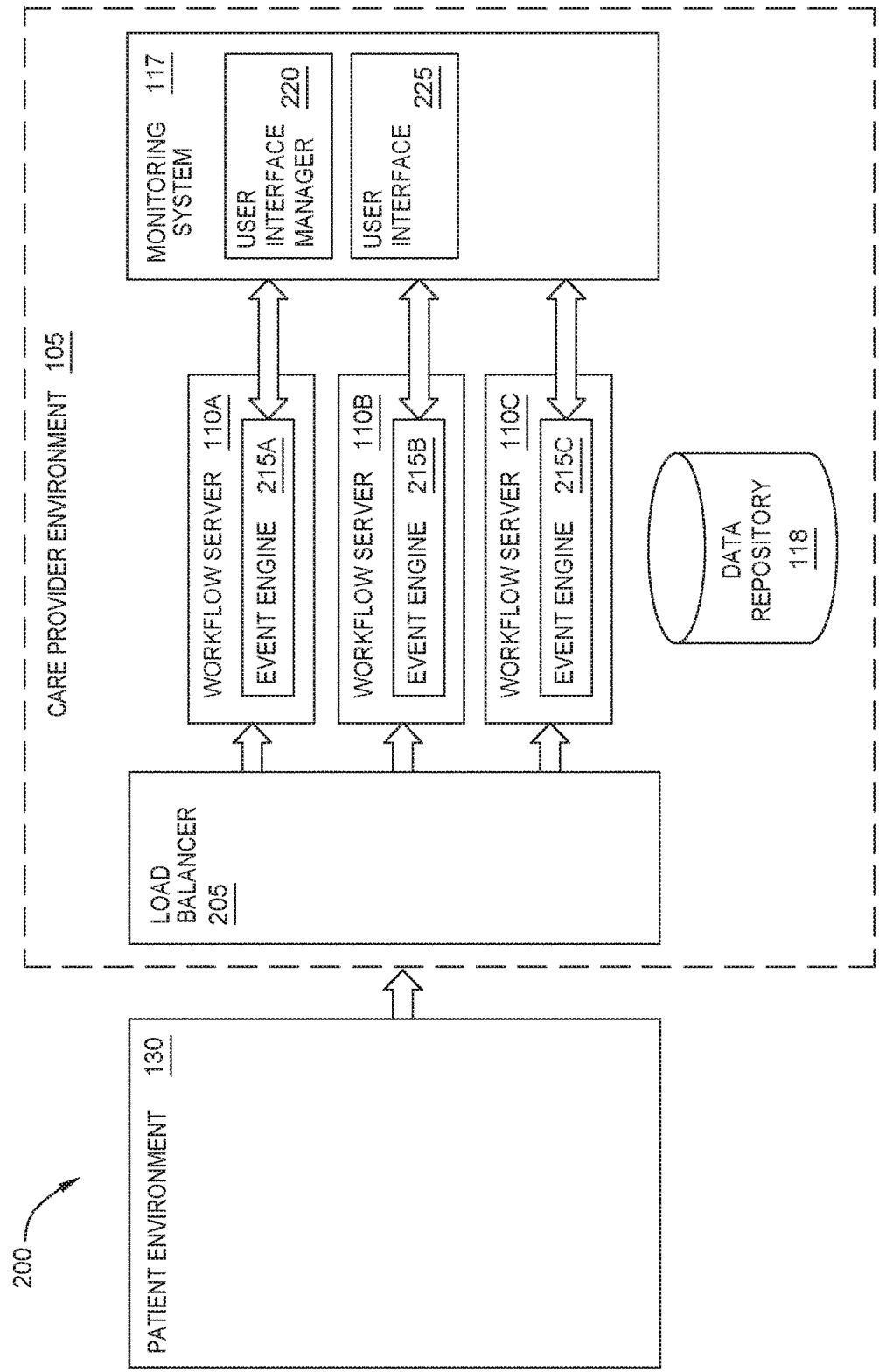
FIG. 2 illustrates a parallel processing computing environment, according to one embodiment described herein.

FIG. 2 illustrates a parallel processing computing environment 200, according to one embodiment described herein. As shown, the patient environment 130 transmits biometric data and/or health events to the care provider environment 105 which includes a load balancer 205. The workflow servers 110A-110C each include a respective one of the event engines 215A-215C. Although not shown, each of the event engines 215A-215C includes a plurality of interconnected processing nodes and queues that form a workflow for processing health events as discussed above. In one embodiment, the event engines 215A-215C each includes the same processing nodes and queues arranged in the same manner such that any one of the event engines 215A-215C can process the different health events generated by the at least one sensor device 140—i.e., any one of the event engines 215A-215C can process a cardiac event, respiratory event, maintenance event, etc. Based on current workload, the load balancer 205 transmits received data or heath events to one of the workflow servers 110A-110C for processing. For example, the load balancer 205 may assign the received health events in a round robin manner or by monitoring each respective central processing unit (CPU) or memory usage of the workflow servers 110A-110C.

Alternatively, the event engines 215A-215C may have different processing nodes and queues (or a different arrangement of the nodes and queues) such that the event engines 215A-215C are configured to process different event types. For example, the event engines 215A, 215B may have workflows that process cardiac events (and have the same processing nodes and queues), while the workflow in the event engine 215C processes respiratory events. The load balancer 205 may determine which of the event engines 215A-215C should receive the health event using the initial classification provided by the patient environment 130 or based on which of the at least one sensor device 140 measured the biometric data.

Regardless whether the event engines 215A-215C have the same arrangement or different arrangements, compute resources can easily be adjusted in response to varying workloads. For example, if additional sensor devices (e.g., sensor devices 140) are added to the patient environment 130, a system administrator can add additional ones of the workflow servers 110A-110C to process an increased number of received health events. The reverse is also true. If the number of health events decreases, the administrator may remove one or more of the workflow servers 110A-110C. For example, if the event engines 215A, 215B both process cardiac events but the number of cardiac events has decreased, the system administrator may remove one of the workflow servers 110A, 110B. As another example, a load balancer component could monitor the usage of computational resources by the workflow servers 110A-110C and could scale the number of servers up or down, based on the computational resource usage.

With continued reference to FIG. 2, the monitoring system 117 includes a user interface manager 220 (UI manager) and a user interface 225 (UI). As discussed above, the processing nodes 114 may require input from the care provider 101 (FIG. 1) in order to route the health events through the event engines 215A-215C. To do so, the event engines 215A-215C transmit requests to the UI manager 220 which generates the UI 225 which can be displayed to the care provider 101. For example, the UI manager 220 may generate the UI 225 that includes an electrocardiogram (ECG) chart corresponding to a cardiac event. Further, the UI 225 may include I/O features (e.g., buttons or pull down menus) that the care provider can use to provide input or instructions to one of the event engines 215A-215C. For example, the care provider may instruct the one of the event engines 215A-215C to store the cardiac event in the data repository 118, send the cardiac event to one of the queues 115 (FIG. 1) that is monitored by another care provider (e.g., to get a second opinion), or forward the cardiac event to the care provider 101 of the patient 103. Thus, the monitoring system 117 permits the workflow servers 110 to output information to the care provider 101 as well as receive instructions from the care provider 101.

The event engines 215A-215C may store data in and retrieve data from the data repository 118. For example, the event engines 215 may maintain a patient history by storing all the received health events (or selected health events) derived based on monitoring a patient's vitals in the repository 118. Further, the event engines 215A-215C may use the data stored in the data repository 118 to process the health events. For example, if one of the event engines 215A-215C receives biometric data indicating the current weight of the patient 103, then the one of the event engines 215A-215C can retrieve past weight measurements for the patient 103 from the data repository 118 and derive a trend graph detailing how the weight of the patient 103 has changed over time. For instance, the patient's current weight may not be enough to trigger a health event, but the patient's derived weight change over a period of time may trigger a health event. As discussed below, these derived trends may be used to generate a derived observation (or other event(s)).

In one embodiment, the event engines 215A-215C prioritize health events, which, in turn, determines how quickly the health events are processed by the workflows in the event engines 215A-215C or what processing nodes and queues are used to process the health events. As discussed above, the health events may be prioritized based on a severity of the health event, the type of the health event, a characteristic of the patient 103 whose biometric data generated the health event, and the like. Additionally, the health events could be prioritized based on additional criteria, such as an institutional policy, a care plan-level policy, a patient-level policy, another policy or some combination of the above.

Figure 3:
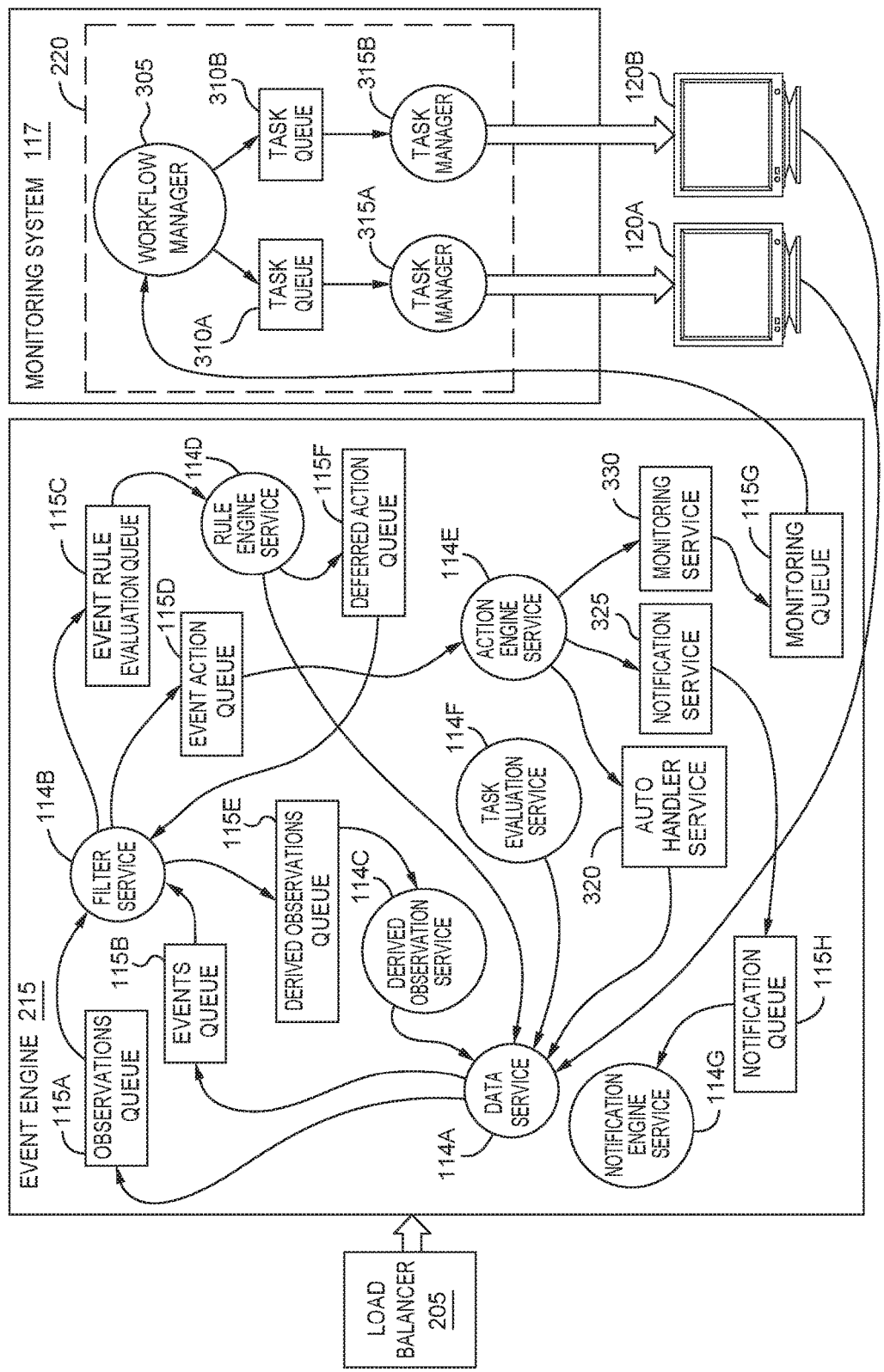
FIG. 3 illustrates an event engine that includes a workflow for processing health events, according to one embodiment described herein.

FIG. 3 illustrates an event engine 215 that includes a workflow for processing health events, according to one embodiment described herein. As described above, a health event or biometric data received from the sensors is forwarded from the load balancer 205 to the event engine 215. Specifically, a data service node 114A in the workflow receives the forwarded information from the load balancer 205. If the load balancer 205 forwards a health event, the data service node 114A classifies the health event based on type (e.g., a cardiac, respiratory, or maintenance event). In some cases, the health event was classified before being received by the data service node 114A. Nonetheless, the data service node 114A may review the data associated with the health event such as ECG data, breathing rate, blood pressure, etc. using more compute intensive techniques to determine whether the initial classification was correct. In another example, the data service node 114A may provide a more detailed classification of the health event than the initial classification. For example, the sensor device may have generated the health event because it detected an irregular heartbeat. However, the data service node 114A may evaluate the heartbeat and classify the health event as a specific cardiac health event—e.g., a ventricular trigeminy event or an atrioventricular block event. The data service node 114A may save the classification of the health event which is used by downstream nodes and queues to process the health event.

Instead of receiving a health event, the data service node 114A may receive raw data or observations from the patient environment. That is, the raw data or observations may not have been evaluated by a sensor device worn by the patient to determine if this data triggers a health event. For example, observation data from a sensor includes blood pressure measurements, weight measurements, ECG data, and the like. As discussed below, the event engine 215 evaluates these observations and can trigger health events which are then processed in the engine 215.

The data service node 114A forwards the observations to the observation queue 115A and the health events to the events queue 115B. A filter node 114B pulls the observations and health events stored in the queues 115A and 115B. This node 114B serves as a gatekeeper that determines where the health events and observations are routed for further processing. When evaluating observations, the filter node 114B may determine whether to ignore (i.e., drop) the observations or forward the observations to a derived observation queue 115E. For example, observations such as low battery signals, start signals indicating a sensor device has started collecting biometric data, or stop signals indicating a sensor device has stopped may be ignored by the filter service node 114B. In contrast, the node 114B may forward observations such as weight measurements, blood pressure measurements, ECG data, and the like to the derived observation queue 115E. In this manner, the filter service node 114B screens the incoming observations to determine whether they should be processed further such as checking for triggering health events.

Observations forwarded by the filter service node 114B are then processed by a derived observation service node 114C. This node 114C uses received observations in conjunction with previously received observations to create new observations or to generate a new health event. Stated differently, the derived observation service 114C may aggregate previously received observations with the currently received observations to compute statistics, trends, trigger health events, and the like. Although not shown, node 114C may be communicatively coupled to the data repository which stores past observations. For example, if the currently received observation is a weight measurement, the derived observation service node 114C may evaluate this measurement with previous weight measurements to determine a weight change for the patient over a defined period of time. This weight change may trigger a health event which is then forwarded to the data service node 114A for further processing. Even if a health event is not triggered, the derived observation service node 114C may store a derived observation (e.g., a weight change, average blood pressure, heart rate trends, etc.) in the data repository so that this data is available when further observations for the patient are received by the event engine 215 (or other event engines 215).

In one embodiment, health events may be processed by the derived observation service node 114C. For example, a sensor device may trigger a health event upon determining a patient's average blood pressure for a day exceeds a threshold. The filter service node 114B may forward this health event to the derived observation service node 114C which then may use past blood pressure measurements for that patient to derive a weekly or monthly average blood pressure for the patient, or a blood pressure trend graph. Based on this derived observation, the node 114C may generate a new health event or decide to drop the health event if the derived observation does not satisfy a corresponding condition.

Further, filter service node 114B also includes logic for determining whether received health events should be dropped, forwarded to an event action queue 115D, or forwarded to the event rule evaluation queue 115C. For example, a system administrator may determine that some health events are not relevant for certain patients. The logic in the filter service node 114B may identify and drop these health events to prevent them from propagating through the rest of the event engine 215. For instance, a patient may have a heart murmur that constantly results in a sensor device triggering a health event. Rather than continually processing these health events, a care provider can instruct the filter service node 114B to screen out (or suppress) these health events from the patient.

If a received health event has a corresponding action or actions, the filter service nodes 114B forwards the health event to the event action queue 115D. However, if the action for a health event has not yet been identified, the filter service node 114B forwards the health event to the event rule evaluation queue 115C. A rule engine service node 114D pulls the health events from the queue 115C and evaluates the health event using one or more rules. Example rules include determining whether daily weight change and average blood pressure exceed respective thresholds. Based on this evaluation, the node 114D may determine what action the event engine 215 should perform—e.g., suppress/ignore the event, auto handle the event, display the event to a care provider, or delay processing the event. Once the action is determined, the rule engine service node 114D generates and forwards a new health event that includes the corresponding action to the data service node 114A. Now that the corresponding action is known, once the new health event reaches the filter service node 114B, it forwards the event to the event action queue 115D rather than the event rule evaluation queue 115D.

The rule engine service node 114D may delay processing the health event by forwarding the event to a deferred action queue 115F. The node 114D may do so when there is not enough available computing power to perform the rule evaluation or if the rule evaluation has not yet completed. That is, if all of the rules have not yet been evaluated and further evaluation is required before triggering the event action, then the event may be placed in queue 115F. For example, the rule may trigger a cardiac event but the system must first check to determine if that event is suppressed for the patient before taking the corresponding action. As shown, the health events stored in the deferred action queue 115F are then retrieved by the filter service node 114B and can be reintroduced into the event rule valuation queue 115C at a later time—i.e., when all the rules have been evaluated.

Once a corresponding action for a health event is known and the health event is stored in the event action queue 115D, an action engine service node 114E routes the health event to the appropriate action service—i.e., auto handler service 320, notification service 325, or monitoring service 330. The auto handler service 320 may perform actions that do not require supervision or input by a care provider—e.g., stores the health event in the data repository. As another example, the auto handler service 320 may assign a priority or severity to the health event before the event is reintroduced into the workflow with the new priority. The auto handler service 320 may also generate a new health event when, for example, a health event shows a cardiac event but the data quality is low. In response, the service 320 may introduce a maintenance event for checking the sensor connection/electrodes.

The event engine 215 uses notification service 325 to send information to the patient, a care giver, car provider, or device regarding the health event. The notification service 325 may include different communication channels or techniques for communicating with the patient such as email, chat, SMS messages, etc. Although FIG. 3 illustrates only one notification queue 115H and notification engine service node 114G for handling requests, the event engine 215 may have different queues and notification nodes for the different communication techniques. For example, if a maintenance event is triggered when an electrode is unplugged from a sensor device, the notification service 325 may transmit an email to the patient's mobile device instructing the patient to plug in the electrode. Alternatively, if a respiratory event is triggered because of an elevated breathing rate, the notification service may send an SMS message to the patient asking her if she is currently performing a physical activity.

The monitoring service 330 communicatively couples the event engine 215 to the monitoring system 117. When input from a care provider regarding a health event is desired, the monitoring service 330 forwards the health event to a monitoring queue 115G. The UI manager 220 in the monitoring system 117 includes a workflow manager node 305 that pulls health events from the monitoring queue 115G and assigns them to either task queue 310A or 310B. The UI manager 220 also includes task manager nodes 315A and 315B which generate UIs for the health events. These UIs are then displayed to care providers via the computing devices 120A and 120B. Further, the task manager nodes 315 may place the biometric or maintenance data associated with the health events in the UIs. For example, a UI for a cardiac event may display an ECG graph and a baseline chart, while a UI for respiratory event displays a breathing rate and oxygen levels in the blood. In this manner, the UI manager 220 can generate a customized UI for the different health events.

The computing devices 120 may transmit information to the data service node 114A of the event engine 215 which can be used to generate new health events or update current health events. For example, the care provider may instruct the event engine 215 to take a certain action such as forwarding the health event to a different care provider to get a second opinion, reclassifying the health event, suppressing or ignoring the health event, notifying a health care provider, and the like. Based on the care provider's input, the event engine 215 again routes the health event through the nodes 114 and queues 115.

The event engine 215 also includes a task evaluation service node 114F. Unlike the other nodes and queues in event engine 215 which process or store observation data or health events received from the patient environment, the task evaluation service node 114F determines whether to trigger a health event based on a care protocol or care plan. In one embodiment, the node 114F triggers a health event when the patient does not follow the care protocol or plan. For example, the care protocol may ask that the patient wear a sensor device for certain amount of time during the day or take weight measurements each day. By monitoring the observation and health events received by the event engine 215, the task evaluation service node 114F determines whether the patient has complied with the care protocol. If not, the task evaluation service node 114F triggers a health event with a corresponding action for the event engine 215 to perform such as sending a notification to the patient using notification service 325 or informing a care provider using the monitoring service 330.

Heartbeat Detection Architecture

Figure 4B:
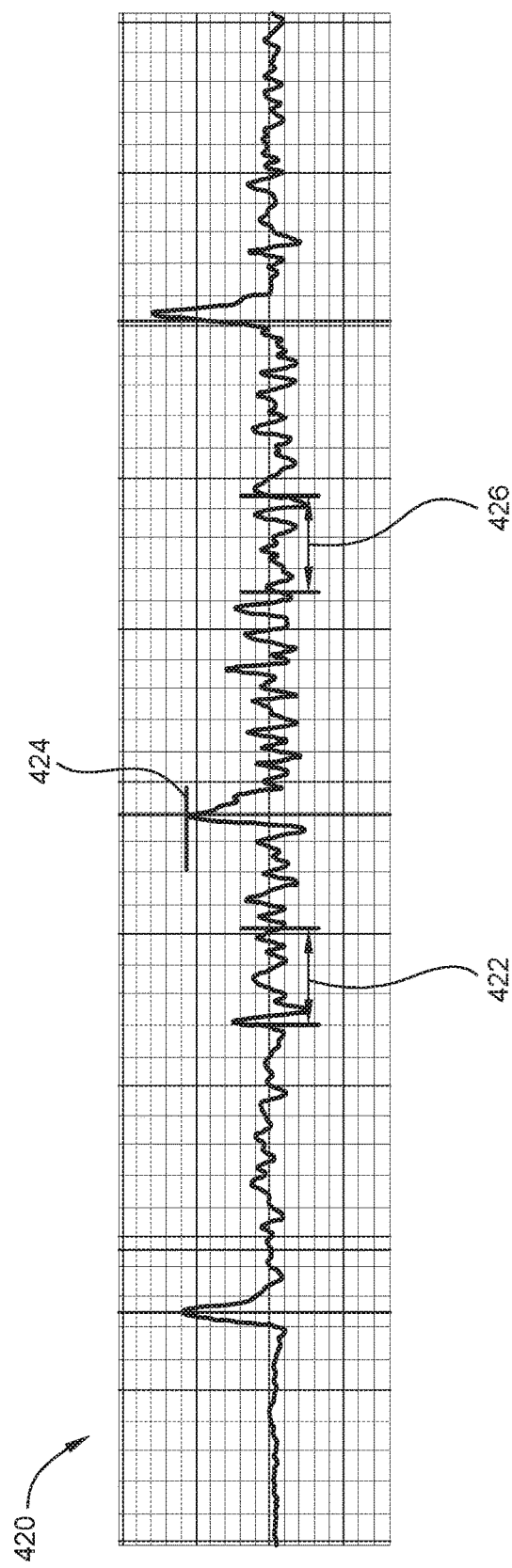
Figure 4C:
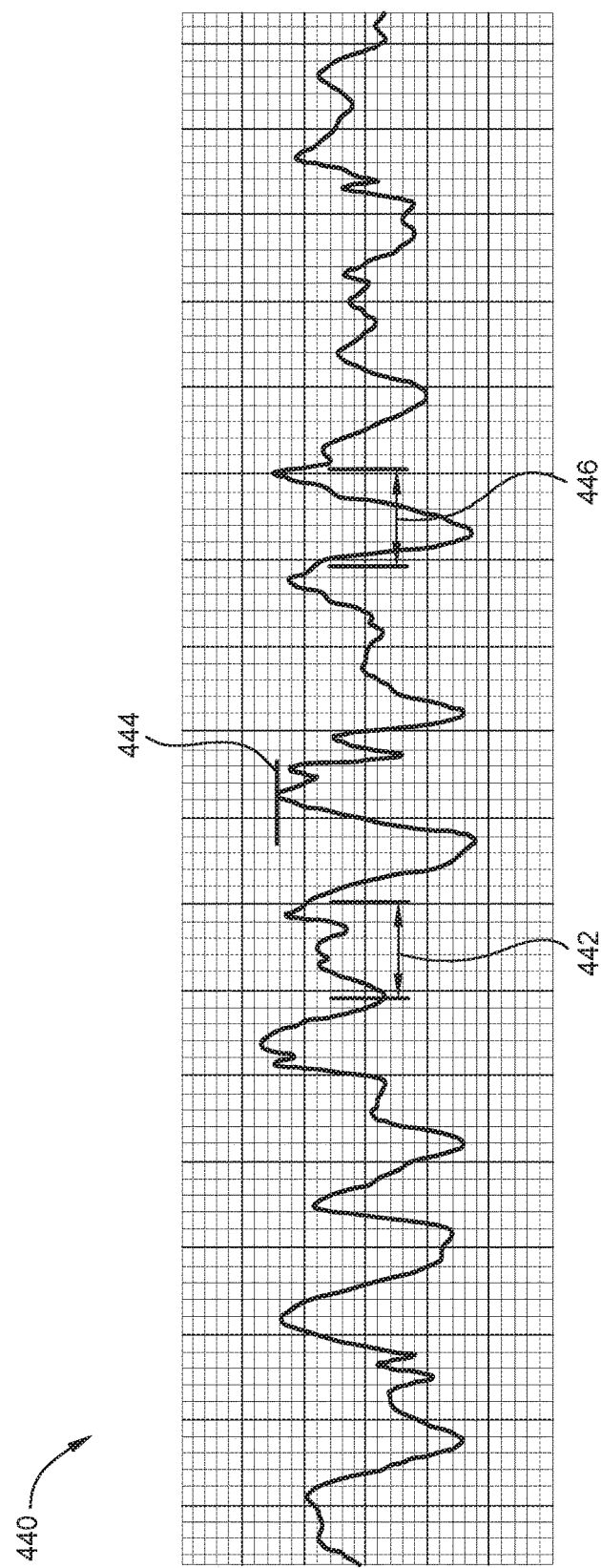

FIG. 4A-C illustrate ECG data, according to one embodiment described herein. In an embodiment, FIG. 4A illustrates ECG data 400 with a relatively high SNR. In an embodiment, the "signal" in the SNR can relate to the amplitude of an R wave in a detected heartbeat in the ECG data 400. The "noise" in the SNR relates to waveform values before and after the detected heartbeat, which in an ideal system would approach zero. In an embodiment, as discussed further below in relation to FIG. 7, the noise excludes P and T waves in the ECG data (e.g., occurring before and after the R wave for the heartbeat) to avoid an inaccurate SNR.

As discussed further below in relation to FIGS. 5 and 6, the SNR for the ECG data illustrated in FIG. 4A can be calculated by comparing the amplitude of the peak of an R wave for a detected heartbeat with the amplitude of surrounding baseline regions. For example, the amplitude at point 404 can represent the amplitude of an R wave for a detected heartbeat. This can be compared with the average amplitude across a region 402, occurring before the detected heartbeat, and a region 406, occurring after the detected heartbeat. In an embodiment, because the ECG data 400 has a relatively high SNR, the ECG data is likely to be more reliable, and automated algorithms analyzing the ECG data (e.g., heartbeat detection and classification algorithms) are likely to be more reliable.

In an embodiment, FIG. 4B illustrates ECG data 420 with a SNR lower than the ECG data 400 illustrated in FIG. 4A. For example, the amplitude at point 424 can represent the amplitude of an R wave for a detected heartbeat. This can be compared with the average amplitude across a region 422, occurring before the detected heartbeat, and a region 426, occurring after the detected heartbeat. As illustrated in FIG. 4B, the peak 424 has a relatively lower amplitude in the ECG data 420 compared to the peak 404 illustrated in FIG. 4A. Further, the regions 422 and 426 include more noise. As discussed further in relation to FIGS. 5 and 6, this results in a lower SNR and a lower confidence in the ECG data 420.

In an embodiment, FIG. 4C illustrates ECG data 440 with a SNR lower than the ECG data 400 illustrated in FIG. 4A and the ECG data 420 illustrated in FIG. 4B. For example, the amplitude at point 444 can represent the amplitude of an R wave for a detected heartbeat. This can be compared with the average amplitude across a region 442, occurring before the detected heartbeat, and a region 446, occurring after the detected heartbeat. As illustrated in FIG. 4C, the peak 444 has a relatively lower amplitude in the ECG data 440 compared to the peak 404 illustrated in FIG. 4A and the peak 424 illustrated in FIG. 4B. Further, the regions 442 and 446 include more noise. As discussed further in relation to FIGS. 5 and 6, this results in a lower SNR and a lower confidence in the ECG data 440. In an embodiment, the ECG data 440 illustrated in FIG. 4C has a low enough SNR to be largely useless in detecting and classifying heartbeats.

Figure 5:
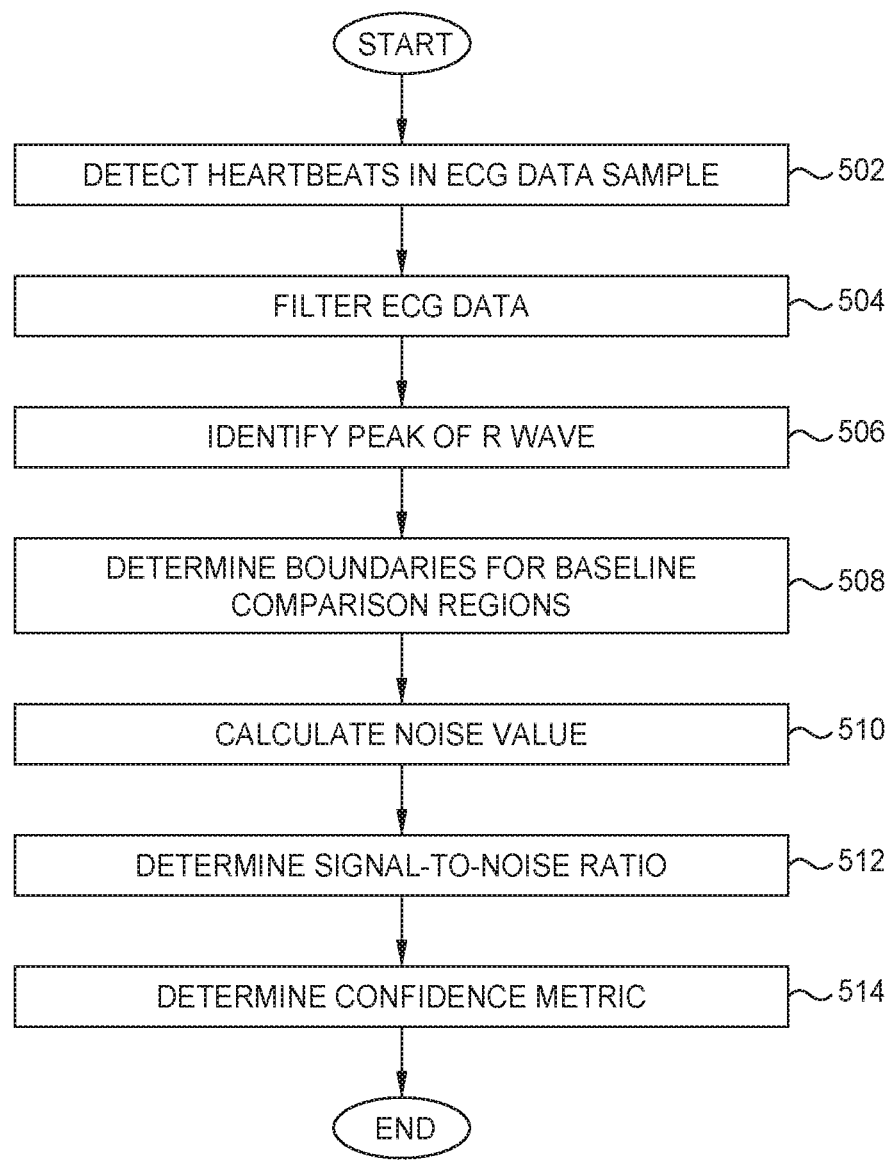
FIG. 5 is a flowchart illustrating determining a determining and using a signal-to-noise ratio for ECG data, according to one embodiment described herein, according to one embodiment described herein.
Figure 6:
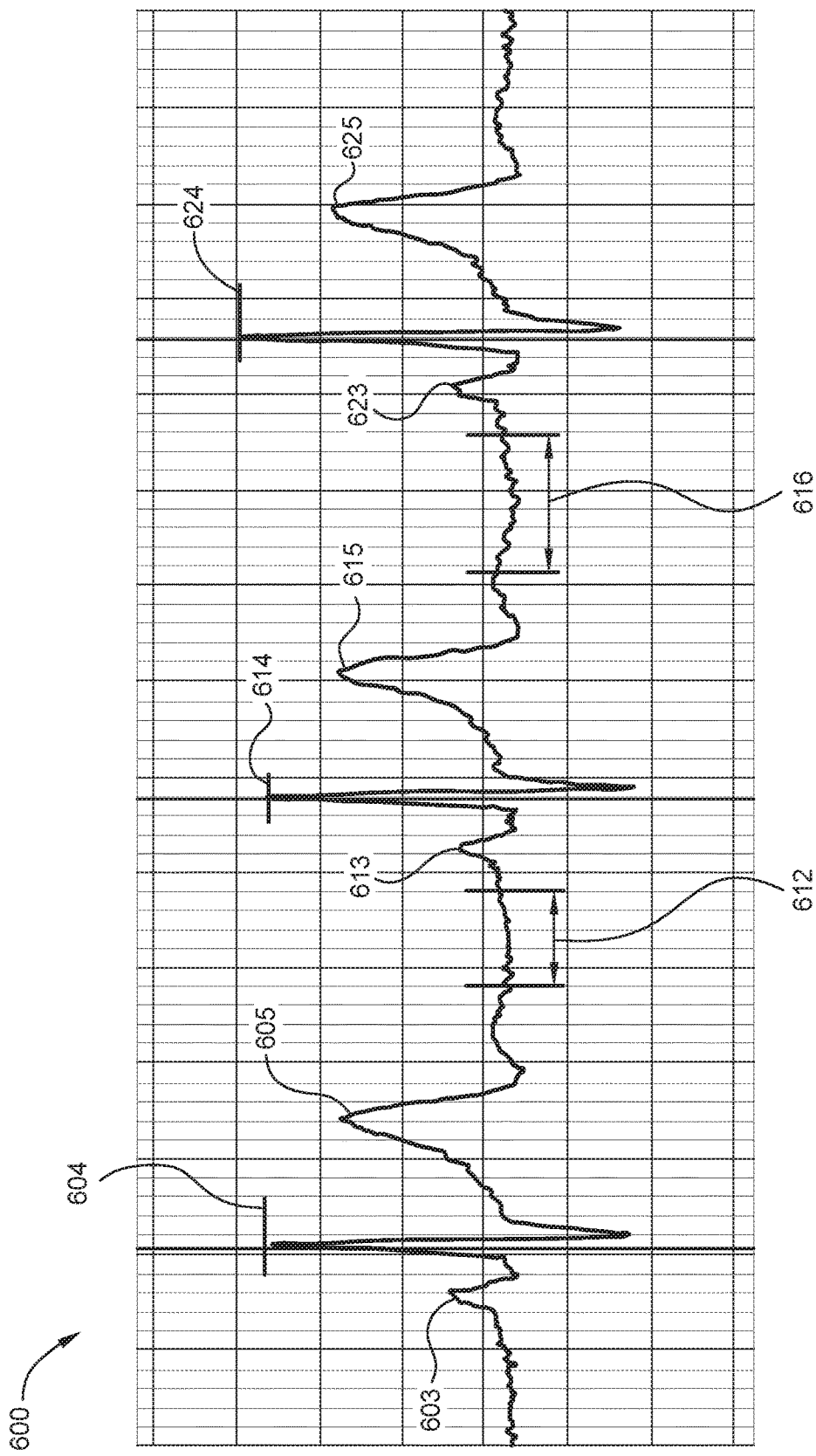
FIG. 6 illustrates determining a signal-to-noise ratio (SNR) for ECG data, according to one embodiment described herein.

FIG. 5 is a flowchart illustrating determining and using a SNR for ECG data, according to one embodiment described herein. FIG. 6 illustrates determining a SNR for ECG data, according to one embodiment described herein. For ease of illustration, these Figures are discussed together.

As discussed below, in one embodiment the techniques illustrated in FIGS. 5-8 are performed using a monitoring application (e.g., the monitoring application 136 illustrated in FIG. 1) on a patient mobile device (e.g., the mobile device 135 illustrated in FIG. 1). Alternatively, the techniques illustrated in FIGS. 5-8 could be partially, or completely, performed on a sensor device (e.g., a body sensor 141 illustrated in FIG. 1). In an embodiment, the techniques illustrated in FIGS. 5-8 are well-suited for the mobile device and sensor device because they require relatively little processing power and use relatively little battery power. This allows the mobile device or sensor device (or both) to determine the SNR and a confidence metric for the ECG data, even if the devices have relatively little processing capability themselves, and without using up the battery life of these mobile devices. Further, this facilitates rapid classification and diagnosis by these devices, before transmitting the data to a care provider environment or server. As another alternative, the techniques illustrated in FIGS. 5-8 could be partially, or completely, performed in a centralized care provider environment (e.g., the care provider environment 105 illustrated in FIG. 1) or on another centralized server.

At block 502, a monitoring application (e.g., the monitoring application 136 illustrated in FIG. 1) detects heartbeats in an ECG data 600. In an embodiment, this can be done using any suitable automatic heartbeat detection algorithm or technique. In an embodiment, the ECG data 600 represents a snippet of ECG data for a patient over a time period.

At block 504, the monitoring application filters the ECG data 600. For example, the monitoring application can apply a high-pass filter to the ECG data 600. In an embodiment, this removes baseline drift, which could result in a false impression of a higher amplitude for the peak and baseline data.

At block 506, the monitoring application identifies the peak of an R wave for the detected beat in the ECG data 600. In an embodiment, this is illustrated as the point 614 illustrated in FIG. 6. In an embodiment, the amplitude of this point 614 is the signal for purposes of calculation of the SNR, as discussed further in relation to block 512, below.

At block 508, the monitoring application determines boundaries for baseline comparison regions. This is discussed further in relation to FIG. 7, below. In an embodiment, the selected baseline comparison regions are region 612, occurring before the detected heartbeat, and region 616, occurring after the selected heartbeat.

At block 510, the monitoring application calculates the noise value. In an embodiment, the noise value is the average amplitude of the signal in at least a portion of the baseline comparison regions. For example, the noise illustrated in FIG. 6 is the average amplitude of the signal in the regions 612 and 616. In an embodiment, the monitoring application calculates the average of the absolute values of the amplitude of the signal in the appropriate region. In some circumstances, noise can result in both upward and downward swings. Averaging the raw amplitude values could result in an artificially low average, masking the noise. Using the average of the absolute values of the amplitude reflects the underlying noise.

At block 512, the monitoring application determines the SNR. In an embodiment, the SNR is calculated using the formula: $SNR=10*\log(signal^2/noise^2)$. For example, as discussed above, signal is the amplitude at the point 614 (e.g., the peak of the R wave for the detected heartbeat) and noise is the average amplitude of the ECG signal in a portion of the regions 612 and 616. This formula, however, is merely one example of a way to calculate SNR for the ECG data 600. Any suitable formula or technique could be used.

At block 514, the monitoring application determines a confidence metric for the ECG data 600. In an embodiment, the monitoring application uses the SNR calculated at block 512 to determine the confidence metric. This is discussed further in relation to FIG. 8, below.

Figure 7:
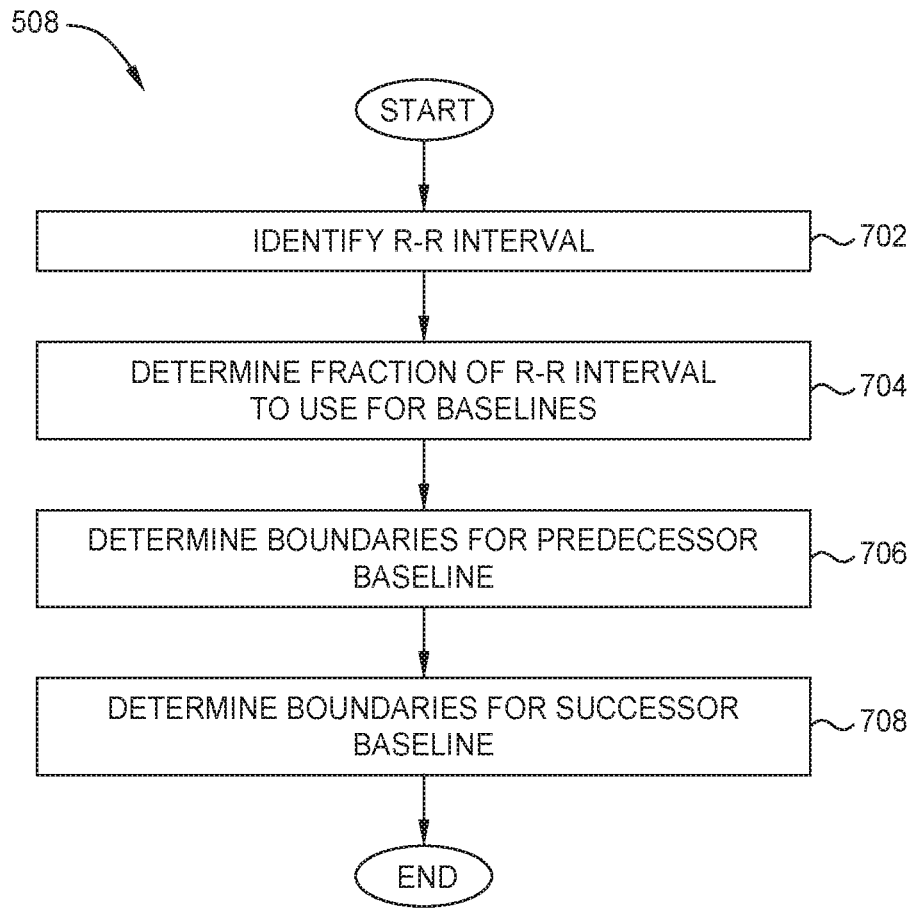
FIG. 7 is a flowchart illustrating determining boundaries for baseline comparisons when determining a SNR for ECG data, according to one embodiment described herein.

FIG. 7 is a flowchart illustrating determining boundaries for baseline comparisons when determining SNR for ECG data, according to one embodiment described herein. In an embodiment, FIG. 7 corresponds with block 508 illustrated in FIG. 5. In general, ECG data represents a recording of electrical activity in the heart over a period of time. A normal sinus rhythm in a heart includes a series of waves: a P wave, a QRS complex (e.g., a Q wave, an R wave, and an S wave), and a T wave. These waves can represent the contraction of the heart during a heartbeat. In an embodiment, the QRS complex is used to detect a heartbeat. Alternatively, another portion of the ECG data could be used instead of, or in addition to, the QRS complex.

At block 702, the monitoring application identifies an R-R interval between the detected heartbeat and the next heartbeat in sequence. For example, as illustrated in FIG. 6, the point 614 marks the peak of the R wave for the detected heartbeat, while the point 624 marks the peak of the R wave for the next heartbeat in sequence. At block 702 the monitoring application identifies the interval between the points 614 and 624.

At block 704, the monitoring application determines the fraction of the R-R interval to use for the baseline regions. In an embodiment, as discussed above, the baseline regions represent the noise in the SNR for the detected heartbeat. In an embodiment, it is desirable to substantially exclude the P wave and the T wave for the detected heartbeat from these regions. In a typical sinus rhythm, the P wave occurs prior to the QRS complex. The P wave represents atrial depolarization, which results in atrial contraction. The T wave occurs following the QRS complex. The T wave represents repolarization of the ventricles. For example, as illustrated in FIG. 6, a P wave 613 precedes the QRS complex with the peak marked by 614. A T wave 615 then follows the QRS complex. Including the P wave 613 or the T wave 615 in the baseline regions 612 and 616 could reduce the accuracy of the SNR calculation. Thus, the baseline regions 612 and 616 substantially exclude the P and T waves.

In an embodiment, at block 704 the monitoring application identifies fractions of the R-R interval to use for the baseline regions in order to exclude the P wave and the T wave. For example, the monitoring application can identify regions between the T wave for one heartbeat and the P wave for the next heartbeat as the baseline regions. As illustrated in FIG. 6, this ECG data 600 represents three heartbeats. The first heartbeat includes a P wave 603, R wave peak 604, and T wave 605. The next heartbeat includes a P wave 613, R wave peak 614, and T wave 615. The last heartbeat includes a P wave 623, R wave peak 624, and T wave 625. The monitoring application selects the baseline region 612 to be between the T wave 605 for the first heartbeat and the P wave 613 for the middle heartbeat. The monitoring application selects the baseline region 616 to be between the T wave 615 for the middle heartbeat and the P wave 623 for the last heartbeat.

In an embodiment, at block 704 the monitoring application excludes the P wave and T wave by assigning fractions of the R-R interval to these waves and excluding those fractions. In an embodiment, these fractions are empirically determined and pre-configured. For example, it could be empirically determined that a T wave takes 50% of the R-R interval in a normal sinus rhythm, while a P wave takes 35% of the R-R interval. These fractions of the R-R interval can then be excluded from the baseline region for the SNR calculation.

Alternatively, the fractions of the R-R interval to use in determining the baseline regions could be determined dynamically. For example, the monitoring application could analyze patient specific ECG data to determine the P wave and T wave durations for that patient. This could be particularly applicable if the monitoring application is implemented in a central server (e.g., the care provider environment 105 illustrated in FIG. 1), which may have access to more data for a particular patient (or class of patient) and which may have more processing capability than a mobile device or sensor device.

At block 706, the monitoring application determines the boundaries for the predecessor baseline region. For example, as illustrated in FIG. 6, at block 706 the monitoring application determines the boundaries for the baseline region 612 (which precedes the R wave peak 614). As discussed in relation to block 704, the monitoring application determines the fraction of the R-R interval (e.g., between 604 and 614 in FIG. 6) likely to be taken up by the T wave 605 and the P wave 603. This fraction is used to identify the boundaries of the baseline region 612: the portion of the ECG data made up of the T wave 605 is excluded, as is the portion of the ECG data made up of the P wave 613. The region between these waves forms the boundaries of the baseline region 612.

At block 708, the monitoring application determines the boundaries for the successor baseline region. For example, as illustrated in FIG. 6, at block 708 the monitoring application determines the boundaries for the baseline region 616 (which succeeds the R wave peak 614). As discussed in relation to block 704, the monitoring application determines the fraction of the R-R interval (e.g., between 614 and 624 in FIG. 6) likely to be taken up by the T wave 615 and the P wave 623. This fraction is used to identify the boundaries of the baseline region 616: the portion of the ECG data made up of the T wave 615 is excluded, as is the portion of the ECG data made up of the P wave 623. The region between forms the boundaries of the baseline region 616.

In an embodiment, only a portion of each baseline region 612 and 616 is used to calculate the noise value. For example, in one embodiment the baseline region 612 applies to both an SNR calculation for the heartbeat with the R wave peak 614 and for a preceding heartbeat with the R wave peak 604 (e.g., the baseline region 612 is the successor baseline for the heartbeat centered at 604 and the predecessor baseline for the heartbeat centered at 614). Thus, a portion of the region 612 is used for the SNR calculation associated with the R wave peak 614 and a portion is used for the SNR calculation associated with the R wave peak 604. In an embodiment, the baseline region 612 is divided in half, with half the region averaged and used to determine the noise for the SNR calculation associated with the R wave peak 614 and the other half of the region averaged and used to determine the noise for the SNR calculation associated with the R wave peak 604.

Figure 8:
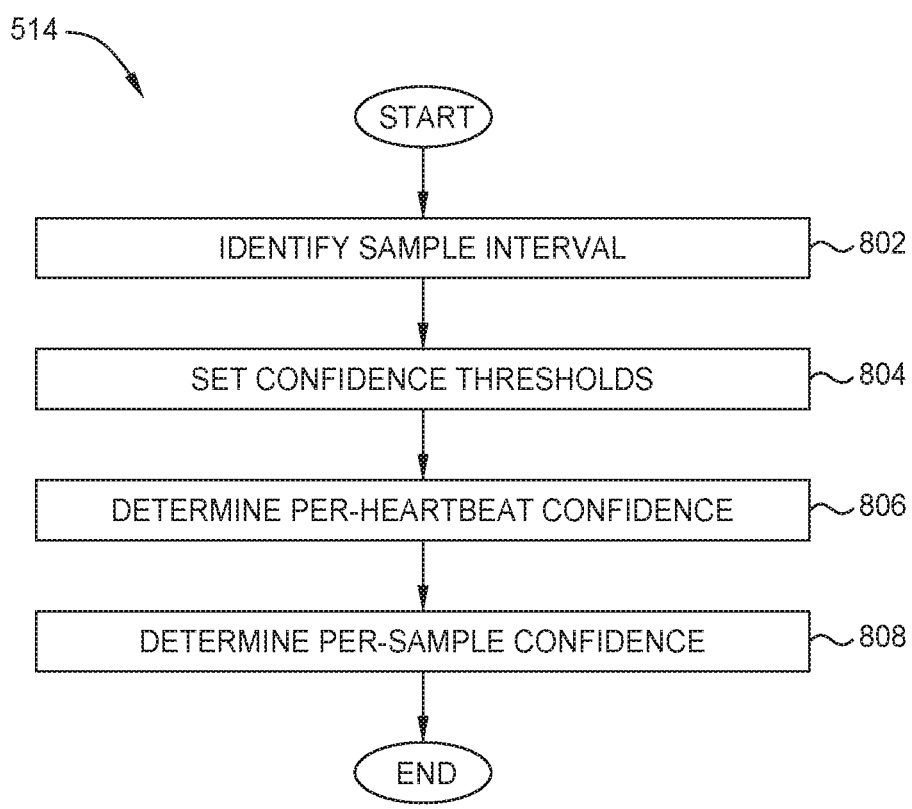
FIG. 8 is a flowchart illustrating determining a confidence metric using a SNR for ECG data, according to one embodiment described herein.

FIG. 8 is a flowchart illustrating determining a confidence metric using a SNR for ECG data, according to one embodiment described herein. In an embodiment, FIG. 8 relates to block 514 illustrated in FIG. 5. At block 802 the monitoring application identifies the sample interval for the ECG data. For example, the monitoring application could select a 10 second snippet of ECG data. Alternatively, shorter, or longer, samples could be used.

At block 804, the monitoring application sets confidence thresholds for the sample. In an embodiment, the monitoring application can use two thresholds: a per-heartbeat threshold and a per-sample threshold. These thresholds can relate to SNR values used to determine confidence in the ECG data. For example, the per-heartbeat threshold can include SNR values to determine the confidence in ECG data for a particular heartbeat. The per-heartbeat threshold can include a single value (e.g., a minimum threshold) or multiple values (e.g., minimum, average, and high confidence thresholds).

As another example, the per-sample threshold can include SNR values to determine the confidence in a given sample of ECG data. In this example, the per-sample threshold can act similarly to the per-heartbeat threshold, for multiple heartbeats in an ECG sample (e.g., by averaging the SNR for multiple heartbeats in a sample, or by considering the minimum or maximum SNR for multiple heartbeats in a sample). The per-heartbeat and per-sample thresholds discussed above are merely examples, and any suitable thresholds could be used. Further, while FIG. 8 illustrates per-heartbeat and per-sample thresholds, in an embodiment only one of these thresholds (or an alternative threshold) is used.

At block 806 the monitoring application determines the per-heartbeat confidence for a given heartbeat in the ECG data sample. For example, the per-heartbeat threshold can include a minimum threshold, an average confidence threshold, and a high confidence threshold. If the SNR for a particular heartbeat falls below the minimum threshold, the monitoring application assigns little or no confidence to the ECG data for that heartbeat. Any detection and classification associated with that heartbeat could be thrown out or excluded from any diagnostic applications.

If the SNR for the heartbeat falls above the minimum but below the average threshold, the monitoring application can assign a low confidence value to the ECG data for that heartbeat. This can be taken into account in diagnostic applications (e.g., automated diagnostic applications) or when providing data to patients and care providers (e.g., providing a confidence level to the care provider). If the SNR for the heartbeat falls above the average threshold but below the high threshold, the monitoring application can assign an average confidence value to the ECG data for that heartbeat. And if the SNR for the heartbeat falls above the high threshold, the monitoring application can assign a high confidence value to the ECG data for that heartbeat. These can again be taken into account in diagnostic applications or when providing data to patients and care providers. These thresholds are merely examples, and any number of suitable thresholds could be used.

Further, the monitoring application can take additional information into account when determining the per-heartbeat confidence. For example, the monitoring application can take into account the patient's heartrate, the classification of the heartbeat, and other factors. In an embodiment, the confidence level in the ECG data for a heartbeat can depend on both the SNR and other factors, including the type of heartbeat detected.

At block 808 the monitoring application determines the per-sample confidence for a given ECG data sample. In one embodiment, the monitoring application could determine the per-sample confidence similarly to the per-heartbeat confidence discussed above in relation to block 806. For example, the monitoring application could average the SNR for multiple heartbeats and compare that to thresholds for an ECG sample (e.g., a minimum, average confidence, and high confidence threshold, as discussed above). As another example, the monitoring application could consider the minimum SNR for multiple heartbeats across a sample, or the maximum SNR.

Alternatively, the monitoring application could use the per-heartbeat confidence for the multiple heartbeats in the sample, as opposed to the SNR. For example, the monitoring application could look for the lowest confidence level for any heartbeat within the sample, and assign that lowest per-heartbeat level as the confidence of the entire sample. As another example, the monitoring application could average the per-heartbeat confidence levels, or could assign the highest confidence level to the entire sample.

Further, the monitoring application can take additional information into account when determining the per-sample confidence. For example, the monitoring application can take into account the patient's heartrate, the classification of the heartbeats, and other factors. In an embodiment, the confidence level in the ECG sample can depend on both the SNR and other factors, including the type of heartbeats detected.

In an embodiment, the confidence metrics for the detected and classified heartbeats are used to inform and treat patients. For example, automated heartbeat detection and classification can identify cardiac irregularities. Devices in the computing environment (e.g., the computing environment 100 illustrated in FIG. 1) can then be used to treat the cardiac irregularity in the patient. For example, a particular medical treatment (e.g., a medication or a patient behavior) for the cardiac irregularity could be recommended to the patient using the patient's mobile device (e.g., the mobile device 135 illustrated in FIG. 1). As another example, a report could be generated for a physician treating the patient, using the classified data. Alternatively, a report could be generated for the patient him or herself. Further, a patient care plan could be generated or modified based on the classified heartbeat. For example, a patient care plan for a patient could be generated based on the classification. The patient care plan could provide medical treatment options (e.g., medication, educational content, behavioral changes, etc.) for the patient based on the classification. Further, an existing care plan for the patient could be modified.

In addition, an alert or output could be generated for the patient, care provider, or other interested parties. For example, an alert could be provided to the patient using a graphical user interface on a device operated by the patient (e.g., a mobile device 135 as illustrated in FIG. 1 or computer). Alternatively, an alert could be provided to the patient's care provider using a graphical user interface on a device operated by the care provider (e.g., a mobile device or a computing device 120 as illustrated in FIG. 1).

All of these medical treatments and notifications can take into account the confidence level in the ECG data. For example, a cardiac irregularity identified using low confidence ECG data might be stored and provided to a patient care provider at a later date, while a cardiac irregularity identified using higher confidence ECG data might be provided immediately to a care provider or might quickly trigger patient medical treatment (e.g., a notification to the patient to sit down, notify a care provider, or take medication). Further, ECG data with lower confidence can be excluded from consideration when deciding medical treatment, or given lower weight.

In an embodiment, one or more techniques disclosed herein can improve identification of critical heartbeats in ECG data. For example, the ECG data for a patient undergoing a serious cardiac event can deviate significantly from ECG data for a normal sinus rhythm. In previous solutions, automated heartbeat detection and classification systems might mistake this deviation for unreliable ECG data or an error in collection, and might exclude the data as unreliable. But using one or more techniques disclosed herein, a monitoring application could determine that the SNR for the ECG data associated with the irregular beat is high, and there is therefore high confidence in the reliability of the ECG data. The monitoring application could then determine that the deviation from the norm likely signified a critical cardiac issue, instead of unreliable data. This allows immediate medical treatment of the patient and emergency notification of care providers, while avoiding false positives from irregular ECG data.

In the preceding, reference is made to embodiments presented in this disclosure. However, the scope of the present disclosure is not limited to specific described embodiments. Instead, any combination of the described features and elements, whether related to different embodiments or not, is contemplated to implement and practice contemplated embodiments. Furthermore, although embodiments disclosed herein may achieve advantages over other possible solutions or over the prior art, whether or not a particular advantage is achieved by a given embodiment is not limiting of the scope of the present disclosure. Thus, the preceding aspects, features, embodiments and advantages are merely illustrative and are not considered elements or limitations of the appended claims except where explicitly recited in a claim(s).

As will be appreciated by one skilled in the art, the embodiments disclosed herein may be embodied as a system, method or computer program product. Accordingly, aspects may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects may take the form of a computer program product embodied in one or more computer readable medium(s) having computer readable program code embodied thereon.

Any combination of one or more computer readable medium(s) may be utilized. The computer readable medium may be a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium is any tangible medium that can contain, or store a program for use by or in connection with an instruction execution system, apparatus or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present disclosure are described below with reference to flowchart illustrations and/or block diagrams of methods, apparatus (systems) and computer program products according to embodiments presented in this disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational blocks to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality and operation of possible implementations of systems, methods and computer program products according to various embodiments. In this regard, each block in the flowchart or block diagrams may represent a module, segment or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

I claim:

1. A computer-implemented method for determining reliability of electrocardiogram (ECG) data, comprising:
receiving ECG data comprising waveform data relating to a detected heartbeat for a patient;
determining a peak amplitude associated with an R-wave in the waveform data, relating to the heartbeat;
identifying a first baseline region in the waveform data and a second baseline region in the waveform data, wherein the first baseline region relates to the heartbeat and precedes the R-wave and the second baseline region relates to the heartbeat and follows the R-wave;
determining a signal-to-noise ratio (SNR) for the waveform data relating to the heartbeat, based on the peak amplitude, the first baseline region, and the second baseline region;
determining a confidence metric relating to the waveform data, based on the determined SNR; and
using the confidence metric in medical treatment related to the patient.

2. The computer-implemented method of claim 1, wherein determining the SNR for the waveform data relating to the heartbeat comprises determining a ratio between the peak amplitude and an average baseline amplitude relating to the first and second baseline regions.

3. The computer-implemented method of claim 2, wherein the average baseline amplitude relating to the first baseline region comprises a first average amplitude across a first portion of the first baseline region and wherein the average baseline amplitude relating to the second baseline region comprises a second average amplitude across a second portion of the second baseline region.

4. The computer-implemented method of claim 3, wherein the SNR for the waveform data is determined using the formula $SNR=10*\log(signal^2/noise^2)$ where the signal relates to the peak amplitude and where the noise relates to the average baseline amplitude.

5. The computer-implemented method of claim 1, wherein identifying the first baseline region in the waveform data and the second baseline region in the waveform data comprises:
identifying an R-R interval in the waveform data;
receiving a fraction of the R-R interval to use in identifying the first baseline region and the second baseline region;
determining a first boundary of the first baseline region in the waveform data using the fraction; and
determining a second boundary of the second baseline region in the waveform data using the fraction.

6. The computer-implemented method of claim 5, wherein the first baseline region substantially excludes a P wave associated with the heartbeat and the second baseline region substantially excludes a T wave associated with the heartbeat.

7. The computer-implemented method of claim 5, wherein the fraction of the R-R interval is pre-configured prior to receiving the ECG data for the patient.

8. The computer-implemented method of claim 1, wherein determining the confidence metric relating to the waveform data, based on the determined SNR, comprises determining at least one of a per-heartbeat confidence metric relating to the heartbeat or a per-sample confidence metric relating to a plurality of heartbeats comprising the heartbeat.

9. The computer-implemented method of claim 1, wherein the confidence metric relating to the waveform data relates to confidence in at least one of automated detection or automated classification of the heartbeat.

10. The computer-implemented method of claim 1, wherein using the confidence metric in medical treatment related to the patient comprises at least one of: (i) providing instructions to the patient relating to the medical treatment, (ii) providing instructions to a care provider for the patient relating to the medical treatment, (iii) providing notification to the patient relating to the detected heartbeat, or (iv) providing notification to the care provider relating to the detected heartbeat.

11. A computer program product for determining reliability of electrocardiogram (ECG) data, the computer program product comprising:
a computer-readable storage medium having computer-readable program code embodied therewith, the computer-readable program code executable by one or more computer processors to perform an operation, the operation comprising:
receiving ECG data comprising waveform data relating to a detected heartbeat for a patient;
determining a peak amplitude associated with an R-wave in the waveform data, relating to the heartbeat;
identifying a first baseline region in the waveform data and a second baseline region in the waveform data, wherein the first baseline region relates to the heartbeat and precedes the R-wave and the second baseline region relates to the heartbeat and follows the R-wave;

determining a signal-to-noise ratio (SNR) for the waveform data relating to the heartbeat, based on the peak amplitude, the first baseline region, and the second baseline region;

determining a confidence metric relating to the waveform data, based on the determined SNR; and using the confidence metric in medical treatment related to the patient.

12. The computer program product of claim 11, wherein determining the SNR for the waveform data relating to the heartbeat comprises determining a ratio between the peak amplitude and an average baseline amplitude relating to the first and second baseline regions.

13. The computer program product of claim 11, wherein identifying the first baseline region in the waveform data and the second baseline region in the waveform data comprises:
identifying an R-R interval in the waveform data;
receiving a fraction of the R-R interval to use in identifying the first baseline region and the second baseline region;
determining a first boundary of the first baseline region in the waveform data using the fraction; and
determining a second boundary of the second baseline region in the waveform data using the fraction.

14. The computer program product of claim 13, wherein the first baseline region substantially excludes a P wave associated with the heartbeat and the second baseline region substantially excludes a T wave associated with the heartbeat.

15. A system, comprising:
a processor; and
a memory storing a program, which, when executed on the processor, performs an operation, the operation comprising:
receiving ECG data comprising waveform data relating to a detected heartbeat for a patient;
determining a peak amplitude associated with an R-wave in the waveform data, relating to the heartbeat;
identifying a first baseline region in the waveform data and a second baseline region in the waveform data, wherein the first baseline region relates to the heartbeat and precedes the R-wave and the second baseline region relates to the heartbeat and follows the R-wave;
determining a signal-to-noise ratio (SNR) for the waveform data relating to the heartbeat, based on the peak amplitude, the first baseline region, and the second baseline region;
determining a confidence metric relating to the waveform data, based on the determined SNR; and
using the confidence metric in medical treatment related to the patient.

16. The system of claim 15, wherein determining the SNR for the waveform data relating to the heartbeat comprises determining a ratio between the peak amplitude and an average baseline amplitude relating to the first and second baseline regions.

17. The system of claim 16, wherein the SNR for the waveform data is determined using the formula $SNR=10*\log(signal^2/noise^2)$ where the signal relates to the peak amplitude and where the noise relates to the average baseline amplitude.

18. The system of claim 15, wherein identifying the first baseline region in the waveform data and the second baseline region in the waveform data comprises:
identifying an R-R interval in the waveform data;
receiving a fraction of the R-R interval to use in identifying the first baseline region and the second baseline region;
determining a first boundary of the first baseline region in the waveform data using the fraction; and
determining a second boundary of the second baseline region in the waveform data using the fraction.

19. The system of claim 18, wherein the first baseline region substantially excludes a P wave associated with the heartbeat and the second baseline region substantially excludes a T wave associated with the heartbeat.

20. The system of claim 15, wherein using the confidence metric in medical treatment related to the patient comprises at least one of: (i) providing instructions to the patient relating to the medical treatment, (ii) providing instructions to a care provider for the patient relating to the medical treatment, (iii) providing notification to the patient relating to the detected heartbeat, or (iv) providing notification to the care provider relating to the detected heartbeat.

* * * * *